(12) United States Patent
Hattori et al.

(10) Patent No.: US 6,495,524 B1
(45) Date of Patent: Dec. 17, 2002

(54) BENZO[B]PYRAN DERIVATIVES USEFUL AS EXTERNAL AGENTS FOR THE SKIN

(75) Inventors: Takao Hattori, Yokohama (JP);
Takayuki Katagiri, Yokohama (JP);
Yoshio Kitada, Yokohama (JP);
Takashi Yoshida, Okayama (JP);
Hideyuki Ito, Okayama (JP)

(73) Assignee: Pola Chemical Industries Inc., Shizuoka (JP)

( * ) Notice: Subject to any disclaimer, the term of this patent is extended or adjusted under 35 U.S.C. 154(b) by 0 days.

(21) Appl. No.: 09/600,617

(22) PCT Filed: Jan. 28, 1999

(86) PCT No.: PCT/JP99/00358
§ 371 (c)(1),
(2), (4) Date: Oct. 10, 2000

(87) PCT Pub. No.: WO99/38858
PCT Pub. Date: Aug. 5, 1999

(30) Foreign Application Priority Data

Jan. 28, 1998 (JP) .............................................. 10-30578
May 28, 1998 (JP) ............................................ 10-164350

(51) Int. Cl.$^7$ .......................... A01N 43/04; A61K 31/70
(52) U.S. Cl. ........................... 514/27; 514/25; 514/456; 536/8; 549/406
(58) Field of Search ........................... 514/456, 25, 27; 549/406; 536/8

(56) References Cited

FOREIGN PATENT DOCUMENTS

JP         06 040883        2/1994

OTHER PUBLICATIONS

Wilson Baker, et al., *Condensation Products of Phenols and Ketones, Part XII Studies with m–Cresol, m–Ethylphenol, and 3:4–Dimethylphenol.*, Journal of the Chemical Society, 1957, pp. 3060–3064.

K. Yamada et al., *The condensation Product of Monomethylammonium 6–Aminosalicylate with Acetone*, Bulletin of the Chemical Society of Japan, vol. 38, No. 12, 1965, pp. 2057–2060.

Svadkovskaya, G.E. et al., *Products formed during the condensation of m–cresol with acetone in the presence of acid catalysts*, Chemical Abstract, vol. 77, No. 19, Nov. 6, 1972.

*Primary Examiner*—Samuel Barts
*Assistant Examiner*—Michael C. Henry
(74) *Attorney, Agent, or Firm*—Knobbe, Martens, Olson & Bear, LLP

(57) ABSTRACT

To provide an external agent for thee skin that not only exhibits excellent effects of prevention and amelioration of skin pigmentation but also has no fear of giving adverse influences to the skin and can be used safely, there is added to an external agent for the skin one or more compound(s) selected from compounds represented by formula (I) below:

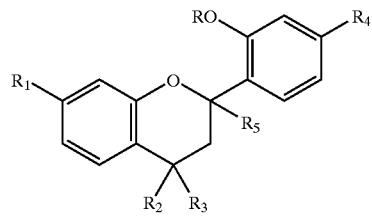

(wherein $R_1$, $R_2$, $R_3$, $R_4$, and $R_5$, independently represent a hydrogen atom or an alkyl group having 1 to 4 carbon atoms; and R represents a hydrogen atom, an acyl group, or a sugar residue).

23 Claims, No Drawings

BENZO[B]PYRAN DERIVATIVES USEFUL AS EXTERNAL AGENTS FOR THE SKIN

This application is the National Phase Application of PCT/JP99/00358, filed Jan. 28, 1999.

TECHNICAL FIELD

The present invention relates to an external agent for the skin and a novel compound that is applicable thereto. More particularly, the present invention relates to an external agent for the skin that contains a compound having an inhibitory activity against melanine synthesis, that is excellent in the prevention and amelioration of skin pigmentation and that is suitable for cosmetics for whitening, and a novel compound having an inhibitory activity against melanine synthesis used preferably thereto.

BACKGROUND ART

Skin pigmentation that causes blotches, freckles, and blackening of the skin after sunburnt is attributed to considerable sthenia of melanine synthesis, which is in turn due to activation of melanocytes in the skin. This is one of problems concerning the skin of middle- to high-aged persons. Accordingly, in order to prevent or ameliorate such a trouble on the skin pigmentation, there have been known external agents far the skin that contain ascorbic acids, aqueous hydrogen peroxide, glutathione, colloidal sulfur, hydroquinone, cathecol or the like.

However, for the prevention and amelioration of skin pigmentation as described above, ascorbic acids tend to be oxidized and thus are unstable and causes discoloration in systems that contain much moisture, such as water-contained cosmetics. Also, aqueous hydrogen peroxide has the problems of stability during storage and safety while glutathione and colloidal sulfur give strong undesirable odors so that their use in products is restricted. Further, those additives such as hydroquinone and cathecol may have the problems of safety, such as skin irritation and allergy. Therefore, there has been currently obtained no external agent for the skin which is satisfactory in the prevention and amelioration of skin pigmentation. That is, there has been a need for a novel external agent for the skin that is safe and has an excellent whitening activity.

On the other hand, among compounds represented by formula (1) used for the external agent for the skin of the present invention, those in which R is a hydrogen atom are known compounds which are described in U. S. Pat. Nos. 2,418,458/1947 and 2,418,459/1947, and the like. Further, it is also known that inulavosin among these compounds has fish toxin activity and antibacterial activity, for example, that for *Staphylococcus aureus, Pseudomonas aeruginosa*, and the like (Heterocycles, Vol. 41, No. 9, 1923–1926 (1995)). However, it has not been known that the compounds represented by formula (I) inclusive of the above compounds have an inhibitory activity against melanine synthesis in skin. Further, it has not been reported that the compounds represented by formula (I) are used for an external agent for the skin to prevent and ameliorate of skin pigmentation.

DISCLOSURE OF THE INVENTION

Under the circumstances, the present invention has been made and an object of the present invention is to provide an external agent for the skin that not only exhibits excellent effects of prevention and amelioration of skin pigmentation but also has no fear of giving adverse influences to the skin and can be used safely.

The term "external agent for the skin" as used herein refers to a composition of any type of formula that can be administered to the skin and be pooled there continuously, used in a broad concept including cosmetics, quasi-drugs, external medicines for the skin and the like.

As a result of intensive investigation with a view to achieve the above-described object, the present inventors have discovered that compounds represented by formula (I), below have strong inhibitory activity against the melanine synthesis by live melanocytes and further that they exhibit excellent effects of prevention and amelioration of skin pigmentation when they are contained in a basic formulation of external agents for the skin. Also, the present inventors have newly produced the compounds having the above-described activity. Based on these, the present invention has been completed.

That is, the present invention relates to an external agent for the skin comprising one or more compound(s) selected from compounds represented by formula (I) below:

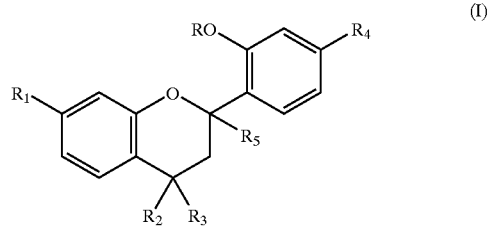

(wherein $R_1$, $R_2$, $R_3$, $R_4$, and $R_5$, independently represent a hydrogen atom or an alkyl group having 1 to 4 carbon atoms; and R represents a hydrogen atom, an acyl group, or a sugar residue).

In a preferred embodiment of the external agent for the skin of the present invention, content of one or more compound(s) selected from the compounds represented by formula (I) ranges in an amount from 0.0045 to 10% by weight based on the total weight of the external agent. The external agent for the skin of the present invention is used advantageously as an external agent for the skin for whitening the skin.

Also, the present invention relates to a compound represented by formula (III) below:

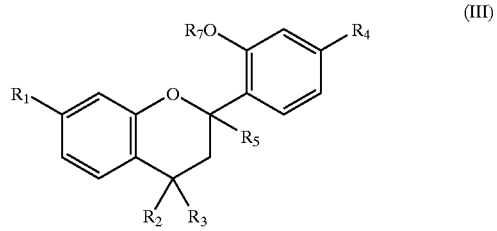

(wherein $R_1$, $R_2$, $R_3$, $R_4$, and $R_5$, independently represent a hydrogen atom or an alkyl group having to 4 carbon atoms; and $R_7$, represents an acyl group or a sugar residue).

Hereafter, the present invention will be described in detail.

(1) Compound represented by formula (I) that is an essential component of the external agent for the skin of the present invention The external agent for the skin of the present invention contains one or more compounds represented by formula (I) above as an essential component. In formula (I), $R_1$, $R_2$, $R_3$, $R_4$, and $R_5$, independently represent a hydrogen atom or an alkyl group having 1 to 4 carbon atoms. The alkyl group having 1 to 4 carbon atoms may be either of a straight or branched chain and specifically includes a methyl group, an ethyl group, a n-propyl group, an isopropyl group, a n-butyl group, a sec-butyl group, or a tert-butyl group, and the like. Among these, a methyl group is particularly preferred.

In formula (I), R represents a hydrogen atom of a hydroxyl group or a substituent of the hydrogen atom of a hydroxyl group, more specifically an acyl group or a sugar residue. Specifically, the acyl group includes an acyl group represented by $R_6$—CO—, wherein $R_6$ represents an alkyl group having 1 to 17 carbon atoms or an alkenyl group having one or two double bonds and 3 to 17 carbon atoms, and mare specifically an acetyl group, a pentanoyl group, an isooctanoyl group, a stearoyl group, an isostearoyl group, an oleoyl group, an octadecadienoyl and the like. The above-described sugar residue is not limited particularly and includes any sugar residue having a glucoside linkage terminal, wherein the sugar is a monosaccharide or disaccharide that can be connected through a glucoside linkage. Specific examples thereof include a glucose residue, a xylose residue, a fructose residue, an arabinose residue, a rhamnose residue, a galactose residue, a sucrose residue, a maltose residue, and the like.

Further, among the compounds represented by formula (I) above, those compounds preferably used for external agent for the skin of the present invention include compounds represented by formula (II) below:

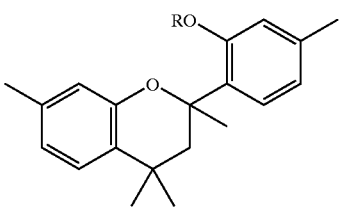

(II)

(wherein R represents a hydrogen atom, an acyl group represented by $R_6$—CO— or a sugar residue; in which $R_6$ represents an alkyl group having 1 to 17 carbon atoms or an alkenyl group having one or two double bonds and 3 to 17 carbon atoms).

The compounds represented by formula (II) above are compounds represented by formula (I) in which $R_1$, $R_2$, $R_3$, $R_4$, and $R_5$ are each a methyl group. Further, as the acyl group or sugar residue represented by R in formula (II), there may be cited the same acyl group or sugar residue in the compounds represented by formula (I) above.

Among the compounds represented by formula (I) above, those in which R is a hydrogen atom are known compounds. Methods for their synthesis are described in U. S. Pat. Nos. 2,418,458/1947 and 2,418,459/1947. The above-described compounds produced by such methods can be used in the present invention.

Further, among the compounds represented by formula (II) that are used advantageously in the present invention, the compound in which R is a hydrogen atom is known as inulavosin. It is also known that the compound has fish toxin activity and antibacterial activity, for example that for *Staphylococcus aureus, Pseudomonas aeruqinosa*, and the like (Heterocycles, Vol. 41, No. 9, 1923–1926 (1995)). Also, inulavosin can be produced by the method as described above.

However, it has not been known that the compounds represented by formula (I) above in which R is a hydrogen atom, inclusive of inulavosin, have an inhibitory activity against melanine synthesis in skin. Further, it has not been known that direct application of the compounds to the skin based on the above-described activity gives rise to so-called whitening effects such as excellent prevention and amelioration of skin pigmentation that would lead to blotches, freckles, blackening of skin after sunburnt or chromatosis such as melanosis. It is believed that the present inventors have found this for the first time.

Further, among the compounds represented by formula (I), the compounds represented by formula (III) below are novel compounds that are not described in the literature. The compounds represented by formula (III) correspond to the acylated compounds or glycosides of the compounds represented by formula (I) above in which R is a hydrogen atom.

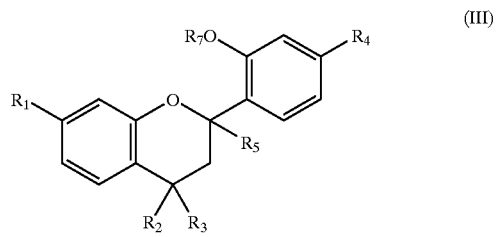

(III)

(wherein $R_1$, $R_2$, $R_3$, $R_4$, and $R_5$, independently represent a hydrogen atom or an alkyl group having 1 to 4 carbon atoms; and $R_7$ represents an acyl group or a sugar residue).

In formula (III) above, examples of $R_1$, $R_2$, $R_3$, $R_4$, and $R_5$, may be cited the same as those for $R_1$, $R_2$, $R_3$, $R_4$, and $R_5$, in formula (I) above. Further, as the aryl group or sugar residue represented by $R_7$, there may be cited the same acyl group or sugar residue in the compounds represented by formula (I) above.

Further, among the novel compounds represented by formula (III) above, those represented by formula (IV) below are compounds that can be used advantageously in the external agent for the skin of the present invention. The compounds represented by formula (IV) correspond to the acylated compounds or glycosides of the above inulavosin.

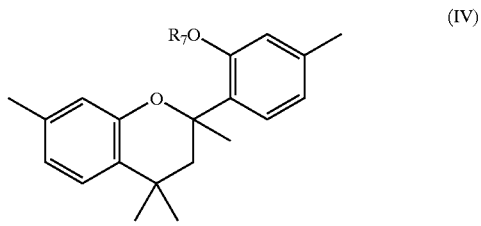

(IV)

(wherein $R_7$, represents an acyl group represented by $R_8$—CO— or a sugar residue; in which $R_8$ represents an alkyl group having 1 to 17 carbon atoms or an alkenyl group having one or two double bonds and 3 to 17 carbon atoms).

The compounds represented by formula (IV) above are compounds represented by formula (III) in which $R_1$, $R_2$, $R_3$, $R_4$, and $R_5$, are each a methyl group. Further, as the acyl group or sugar residue represented by $R_7$ in formula (IV), there may be cited the same acyl group or sugar residue in the compounds represented by formula (III) above.

Further, of these novel compounds, particularly preferred compounds to be applied to the external agent for the skin of the present invention include acetylinulavosin and glycosides of inulavosin.

These novel compounds can be produced by a conventional method using a known compound represented by formula (I) in which R is a hydrogen atom such as inulavosin, for example, by condensation reaction with an acylating agent such as aryl chloride when the targeted compound is an acylated compound, or with a halide of a sugar using silver nitrate or silver oxide as a catalyst when the targeted compound is a glycoside.

(2) External agent for the skin of the present invention

The external agent for the skin of the present invention is characterized by containing one or more compound(s) selected from the compounds represented by formula (I) above. Among the compounds represented by formula (I), preferred for the external agent for the skin of the present invention are inulavosin, acylinuolavosin, and inulavosin glycosides represented by formula (II) above. Of these, inulavosin, acetylinulavosin and inulavosin glucosides are particularly preferred.

In the present invention, addition of one or more compound(s) represented by formula (I) in a basic formulation of external agent for the skin allows exhibition of excellent whitening effect based on the inhibitory activity against melanine synthesis. The content of the above-described compound or compounds ranges preferably in an amount from 0.0005 to 10% by weight based on the total weight of the external agent for the skin. Of course, as stated above, the external agent for the skin of the present invention may include the compounds represented by formula (I) singly or in combination of two or more of them. When two or more of compounds are used in combination, a preferred range of the above-described content may be considered a range of the sum of the contents of the compounds represented by formula (I).

That is, when the external agent for the skin is used for preventing skin pigmentation that would cause blotches, freckles, blackening of skin after sunburnt or chromatosis such as melanosis, its content is desirably 0.0005% or more by weight in point of effect. Further, when the external agent far the skin is used for ameliorating skin pigmentation, its content is preferably 0.1% or more by weight, and more preferably 1% or more by weight in point of effect. As will be apparent from the experimental results described hereinbelow, when the content of the above-described compound is less than 0.0005% by weight, the tendency is observed that the inhibitory activity against melanine synthesis is decreased considerably while in spite of use of the amount of above 10% by weight, the effect reaches a plateau. Therefore, it is desirable that the external agent for the skin of the present invention contains the compound(s) in the above-described range.

Also, the external agent for the skin of the present invention is desirably one that is used in the form in which it is pooled on the skin continuously in view of the characteristics of the compound or compounds activity represented by general formula (I) that the external agent for the skin of the present invention contains as an essential component. In this respect, it can be said that most external agents for the skin conventionally used take application forms desirable for the external agent for the skin of the present invention. Although a washing agent is one embodiment of the external agent for the skin of the present invention, it cannot be said to be a preferred embodiment of the external agent for the skin of the present invention since its application form is temporary in nature, on the other hand, a pack material or the like has a shielding effect, though its contact time with skin is short, so that it is a preferred embodiment of the external agent for the skin of the present invention.

The external agent for the skin of the present invention can be obtained by blending one or more compounds selected from the compounds represented by formula (I) above in a basic formulation far external agents for the skin conventionally used for external agents for the skin, such as external medicines for the skin, cosmetics, and the like by a conventional method and can be produced in the same manner as the conventional external agents for the skin except that one or more compounds selected from the compounds represented by formula (I) above is or are blended therein.

As components of the basic formulation for the above-described external agents for the skin, there can be cited, for example, a moisture component, an oil component, a power component, a surfactant, a tackifier, a colorant, a fragrant, an anti-oxidant, a pH adjusting agent, a chelating agent, a preservative and the like. In addition to the compounds represented by formula (I), the external agent for the skin of the present invention may optionally contain one or more medical components such as a humectant, an ultraviolet shielding agent, and an anti-inflammatory agent. Further, in addition to the compounds represented by formula (I), the external agent for the skin of the present invention may optionally contain one or more whitening components such as a whitening agent, for example, pantetheine-S-sulfonic acid, isoferulic acid, magnesium phosphate ascorbic acid salt, arbutin, kojic acid, rinolic acid, methyl tinplate, and the like.

Further, the application form of the external agent for the skin of the present invention may be of any type conventionally used for this type of external agent for the skin and includes, for example, ointment, cream, emulsion, lotion, pack and the like application forms.

Applications of the external agent for the skin of the present invention include cosmetics, quasi-drugs, external medicine for the skin and the like. Further, the external agents for the skin can be used advantageously for whitening.

EMBODIMENT MODE FOR CARRYING OUT THE INVENTION

Hereafter, the present invention will be described in more detail by examples. However, the present invention should not be construed as being limited thereto.

Production Example 1

Synthesis of Inulavosin (2-hydroxy-2,4,4,7,4'-pentamethylflavan)

12.0 g of m-cresol was dissolved in 100 ml of dry acetone and then hydrogen chloride gas was bubbled therein till saturation under ice cooling condition, followed by standing for 24 hours at room temperature with a stopper. Thereafter, the obtained mixture was cooled with ice again, a small amount of ether was added thereto, and the mixture was rendered strong alkaline by addition of an aqueous solution of 20% sodium hydroxide, followed by vigorous stirring overnight. Next, the reaction mixture thus obtained was neutralized with 1N hydrochloric acid, extracted with ether, and the ether layer was taken out. The ether layer was concentrated and purified by silica gel chromatography. Then the necessary fractions were concentrated and recrystallized from a small amount of ether. Since the crystals obtained were ether-conjugates, they were dried well using a vacuum pump. As a result, 3.0 g of inulavosin was obtained as white powder. NMR measurement of the inulavosin thus obtained gave the following results.

Results of NMR Measurement
H-NMR (in CDCl$_3$); 1.18 (3H,s), 1.42(3H,s), 1.69(3H,s), 2.06(1H,d), 2.26(3H,s), 2.30(3H,s), 2.54(1H,d), 6.65(1H,d), 6.67(1H,s), 6.75(1H,s), 6.81(1H,d), 7.03(1H,d), 7.17(1H,d)

Example 1

Synthesis of Acetylinulavosin (2'-acetoxy-2,4,4,7,4'-pentamethylflavan)

After 5.0 g of inulavosin (2'-hydroxy-2,4,4,7,4'-pentamethylflavan) obtained in Production Example 1 above was dissolved in a mixed solution of 60 ml of pyridine and 40 ml of acetic anhydride and the mixture was left to stand overnight, the reaction mixture was poured into water. The precipitate that formed was recrystallized from ethanol to obtain 4.8 g of acetylinulavosin (2'-acetoxy-2,4,4,7,4'-pentamethylflavan). NMR measurement of the acetylinulavosin thus obtained gave the following results.
Results of NMR Measurement $^1$H-NMR (in CDCl$_3$); 1.18 (3H,s), 1.42(3H,s), 1.69(3H,s), 2.06(1H,d), 2.23(3H,s), 2.26 (3H,s), 2.31(3H,s), 2.54(1H,d), 6.65(1H,d), 6.67(1H,s), 6.77 (1H,s), 6.81(1H,d), 7.04(1H,d), 7.18(1H,d)

Example 2

Synthesis of Glucosylinulavosin (2'—O—glucosyl-2,4,4,7,4'-pentamethylflavan)

5.0 g of inulavosin (2'-hydroxy-2,4,4,7,4'-pentamethylflavan) obtained in Production Example 1 above and 7.0 g of tetra-O-acetyl-glucosyl-bromide were dissolved in 100 ml of dichloromethane, 4.0 g of silver oxide was added thereto, and the mixture was stirred with light shield. After filtration of the silver and concentration of the filtrate, the filtrate was purified by silica gel chromatography to obtain 2'-(tetra-O-acetyl-glucosyl)-2,4,4,7,4'-pentamethylflavan. After this compound was dissolved in methanol and 1N MeONa was added thereto, the mixture was stirred at room temperature to liberate the acetyl group from the above-described compound. After concentration of the reaction mixture, recrystallization from ethanol afforded 6.3 g of glucosylinulavosin (2'-O-glucosyl-2,4,4,7,4'-pentamethylflavan).

NMR measurement of the above obtained 2'-(tetra-O-acetyl-glucosyl)-2,4,4,7,4'-pentamethylflavan gave the following results.
Results of NMR Measurement
$^1$H-NMR (in CDCl$_3$); 1.18 (3H,s), 1.42(3H,s), 1.69(3H,s), 2.02(3H,s), 2.03(3H,s), 2.04(3H,s), 2.06(1H,d), 2.11(3H,s), 2.26(3H,s), 2.30(3H,s), 2.54(1H,d), 3.72(2H,m), 4.20(1H, m), 4.61(1H,d), 5.08–5.32(3H,m), 6.65(1H,d), 6.67(1H,s), 6.74(1H,s), 6.81(1H,d), 7.03(1H,d), 7.17(1H,d)

Example 3

Inhibitory Activity against Melanine Synthesis

To evaluate the potency of the compounds represented by formula (I) of the present invention on the inhibitory activity against the melanine synthesis by melanocytes, the following experiments were conducted.
Method
$3 \times 10^4$ cells of mouse melanoma-derived cells B-16 were inoculated in a plastic incubation flask (75 cm$^3$) and incubated in Eagle MEM medium containing 10% fetal bovine serum under the conditions of 5% CO$_2$ and 37° C. Two days after the start of the incubation, the inulavosin obtained in Production Example 1 above, the acetylinulavosin obtained in Example 1, or the glucosylinulavosin obtained in Example 2 was added to the incubation flask so that its concentration in the medium became $5 \times 10^{-5}$ to $1 \times 10^{-3}$ (W/V%) as shown in Tables 1 to 3 below, and the incubation was continued for additional 4 days. After completion of the incubation, the medium was removed from the incubation flask and the flask was washed with equilibrium phosphate buffer solution (hereinafter referred as "PBS"). Thereafter, the cells adhered on the incubation flask were stripped off with a solution containing trypsin and EDTA and then the obtained mixture was centrifuged to collect the cells.

After washing the collected cells with PBS, 1N sodium hydroxide was added to the precipitate, and the mixture was heat-dissolved. After cooling, chloroform was added thereto and the mixture was stirred and centrifuged again. The resultant supernatant was measured for absorbance at 400 nm and the amount of melanine was obtained by a calibration curve prepared in advance using synthetic melanine. The amount of melanine was obtained as weight ($\mu$g) per 10$^6$ cells. In the experiments, five flasks were used for each concentration of the test samples.

Tables 1 to 3 show the results obtained as average values of five flasks together with standard deviations. Tables 1 to 3 show the results for inulavosin, acetylinulavosin, and glucosylinulavosin, respectively.

In addition, as a control, the amount of melanine was determined by conducting the same experiments as described above except that the compound represented by formula (I) was not added. From the amount of melanine in the absence of samples and the amount of melanine in the presence of a sample, there was obtained melanine synthesis inhibition ratio (R(%)) by the following equation. The amount of melanine in the equation was an average value obtained from five flasks.

$$R(\%) = (A-B) \times 100/A$$

R: Melanine synthesis inhibition ratio
A: Amount of melanine in the absence of samples
B: Amount of melanine in the presence of a sample
The results are shown at most right columns in Tables 1 to 3, respectively.

TABLE 1

| Inulavosin (W/V %) | Amount of Melanine ($\mu$g/10$^6$ cells) | Inhibition Ratio (%) |
| --- | --- | --- |
| No addition | 3.23 ± 0.36 | — |
| 5 × 10$^{-5}$ | 2.74 ± 0.32 | 15.2 |
| 1 × 10$^{-4}$ | 2.23 ± 0.24 | 31.0 |
| 5 × 10$^{-4}$ | 0.87 ± 0.21 | 73.1 |
| 1 × 10$^{-3}$ | 0.28 ± 0.17 | 91.3 |

TABLE 2

| Acetylinulavosin (W/V %) | Amount of Melanine ($\mu$g/10$^6$ cells) | Inhibition Ratio (%) |
| --- | --- | --- |
| No addition | 3.23 ± 0.36 | — |
| 5 × 10$^{-5}$ | 2.93 ± 0.35 | 9.3 |
| 1 × 10$^{-4}$ | 2.42 ± 0.26 | 25.1 |
| 5 × 10$^{-4}$ | 1.22 ± 0.17 | 62.2 |
| 1 × 10$^{-3}$ | 0.39 ± 0.18 | 87.9 |

TABLE 3

| Glucosylinulavosin (W/V %) | Amount of Melanine ($\mu$g/$10^6$ cells) | Inhibition Ratio (%) |
|---|---|---|
| No addition | 3.23 ± 0.36 | — |
| $5 \times 10^{-5}$ | 3.02 ± 0.33 | 6.5 |
| $1 \times 10^{-4}$ | 2.52 ± 0.23 | 22.0 |
| $5 \times 10^{-4}$ | 1.35 ± 0.17 | 58.2 |
| $1 \times 10^{-3}$ | 0.62 ± 0.15 | 80.8 |

As will be clear from the results in Tables 1 to 3, it was demonstrated that inulavosin, acetylinulavosin, and glucosylinulavosin have inhibitory activity against the melanine synthesis by melanocytes and that this activity was remarkable in concentrations of 0.0005 w/v% or more, particularly. Note that no toxicity of the compounds represented by formula (I) to melanocytes was observed during the above experiments. From this it follows that the compounds represented by formula (I) have high safety.

Example 4

Preparation of Oil-in-water Creams

Oil-in-water creams according to the formulation shown in Table 4 below was prepared by the following production method.
Production method
The ingredients in component (A) were combined and heated at 80° C. Also, the ingredients in component (B) were combined and heated at 80° C. The component (B) was added to the component (A) and stirred for emulsification. Thereafter, the mixture was cooled down to 35° C.

TABLE 4

| | Component | Blending Amount (% by weight) |
|---|---|---|
| (A) | POE (30) Cetyl ether | 2.0 |
| | Glycerol monostearate | 10.0 |
| | Liquid paraffin | 10.0 |
| | Vaseline | 4.0 |
| | Cetanol | 5.0 |
| | $\gamma$-Tocopherol | 0.05 |
| | Dibutylhydroxytoluene (BHT) | 0.01 |
| | Butylparaben | 0.1 |
| | Inulavosin | 0.5 |
| (B) | Propylene glycol | 10.0 |
| | Distilled water | 58.34 |

Example 5

Actual Use Test

Next, taking into consideration the test results of the above-described inhibitory activity against the melanine synthesis, actual use tests by long term continuous use were conducted using the oil-in-water creams obtained in Example 4 above in order to demonstrate how the external agent for the skin of the present invention was excellent in the effects of prevention and amelioration of skin pigmentation and their effectiveness was confirmed. As comparative preparation, there was used an oil-in-water cream prepared in the same manner as in Example 4 except that inulavosin was replaced by distilled water.

That is, 40 female volunteers who suffered from dark complexion, blotches, or freckles were divided into two statistically equivalent groups A and B. The group A persons used the oil-in-water cream of Example 4 of the present invention, while the group B persons used the comparative preparation of oil-in-water cream, for 3 months for application to their faces. After 3 months, ameliorating effect against pigmentation was evaluated by naked eyes and inter-group comparison was performed. The evaluation was made based on 5-rank criteria of considerably ameliorated, fairly ameliorated, slightly ameliorated, no change, and aggravated. Table-5 shows the results obtained. The efficiency was a value obtained by judging the persons who got evaluation of slightly ameliorated or of higher rank as effective and counting the number of persons who were effective and then calculating the percentage of the number of effective persons to the total number of the persons constituting the group, i.e., 20.

TABLE 5

| Evaluation | Product of the present invention (Example 4) | Comparative Product |
|---|---|---|
| Considerably ameliorated | 5 | 0 |
| Fairly ameliorated | 7 | 1 |
| Slightly ameliorated | 4 | 2 |
| No change | 4 | 17 |
| Aggravated | 0 | 0 |
| Efficiency (%) | 80% | 15% |

As the results in Table 5 show, it was demonstrated that the external agent for the skin of the present invention has much superior effects of preventing and ameliorating skin pigmentation to the comparative external agent for the skin. In addition, no undesirable response was observed in the skin at the site where the external agent of the present invention was applied, which also confirmed that the external agent for the skin of the present invention is highly safe.

Example 6

Preparation of Emulsion

Emulsion according to the formulation shown in Table 6 was prepared by the following production method.
Production Method
The ingredients in component (A) and the ingredients in component (B) were each dissolved at 70° C. with stirring. The component (A) was added to the component (H) and preliminarily emulsified and then uniformly emulsified using a homomixer. After the emulsification, the emulsion was cooled to 30° C. with stirring.

TABLE 6

| | Component | Blending Amount (% by weight) |
|---|---|---|
| (A) | Synthetic spermaceti | 2.5 |
| | Cetanol | 1.0 |
| | Squalane | 4.0 |
| | Stearic acid | 1.0 |
| | Monosteraric acid polyethylene glycol (25EO) | 2.2 |
| | Glycerol monostearate | 0.5 |
| | Butylparaben | 0.1 |
| | $\gamma$-Tocopherol | 0.05 |
| | BHT | 0.01 |
| | 4-(1,1-Dimethylethyl)-4'-methoxy-benzoylmethane | 0.5 |
| | Inulavosin | 1.0 |

TABLE 6-continued

| | Component | Blending Amount (% by weight) |
|---|---|---|
| (B) | 1,3-Butylene glycol | 3.0 |
| | Propylene glycol | 7.0 |
| | Xanthan gum | 0.1 |
| | Carboxyvinylpolymer | 0.2 |
| | Potassium hydroxide | 0.2 |
| | Distilled water | 76.64 |

Example 7

Preparation of Lotion

Lotion was prepared according to the formulation shown in Table 7 by the following production method.

Production Method

The ingredients in component (A) were combined and dissolved at room temperature. On the other hand, the ingredients in component (B) were dissolved at room temperature. The component (B) was added to the component (A) to solubilize it.

TABLE 7

| | Component | Blending Amount (% by weight) |
|---|---|---|
| (A) | POE(20) Sorbitan monolaurate | 1.5 |
| | POE(20) lauryl ester | 0.5 |
| | Ethanol | 10.0 |
| | γ-Tocopherol | 0.02 |
| | Inulavosin | 0.25 |
| (B) | Glycerol | 5.0 |
| | Propylene glycol | 4.0 |
| | Sodium isoferulate | 0.5 |
| | Citric acid | 0.15 |
| | Sodium citrate | 0.1 |
| | Distilled water | 77.98 |

Example 8

Preparation of Pack Material

A pack material was prepared according to the formulation shown in Table 8 by the following production method.

Production method

The ingredients in component (A) were dispersed and dissolved at room temperature. On the other hand, the ingredients in component (B) were dissolved at room temperature. The component (H) was added to the component (A) and uniformly dissolved.

TABLE 8

| | Component | Blending Amount (% by weight) |
|---|---|---|
| (A) | Polyvinyl alcohol | 15.0 |
| | Distilled water | 40.0 |
| (B) | Bisabolol | 0.5 |
| | γ-Tocopherol | 0.02 |
| | Ethanol | 4.0 |
| | Inulavosin | 3.0 |
| | POE(8) Polyoxypropylene glycol (55) | 3.0 |
| | Distilled water | 34.48 |

Example 9

Preparation of Oil-in-Water Cream

An oil-in-water cream was prepared according to the formulation shown in Table 9 by the following production method.

Production Method

The ingredients in component (A) were combined and heated at 80° C. Also, the ingredients in component (B) were combined and heated at 80° C. The component (B) was added to the component (A) and stirred for emulsification. Thereafter, the mixture was cooled down to 35° C.

TABLE 9

| | Component | Blending Amount (% by weight) |
|---|---|---|
| (A) | POE(30) Cetyl ether | 2.0 |
| | Glycerol monostearate | 10.0 |
| | Liquid paraffin | 10.0 |
| | Vaseline | 4.0 |
| | Cetanol | 5.0 |
| | γ-Tocopherol | 0.05 |
| | Dibutylhydroxytoluene(BHT) | 0.01 |
| | Butylparaben | 0.1 |
| | Glucosylinulavosin | 0.5 |
| (B) | Propylene glycol | 10.0 |
| | Distilled water | 58.34 |

INDUSTRIAL APPLICABILITY

The external agent for the skin of the present invention exhibits excellent effects of preventing or ameliorating skin pigmentation attributed to the excellent inhibitory activity of the compounds represented by formula (I) against the melanine synthesis. Further, the above-described compounds have no fear in safety so that it can be said that there is no problem in safety in using the external agent for the skin of the present invention.

What is claimed is:

1. An external agent for the skin comprising one or more compounds) selected from compounds represented by formula (I) below:

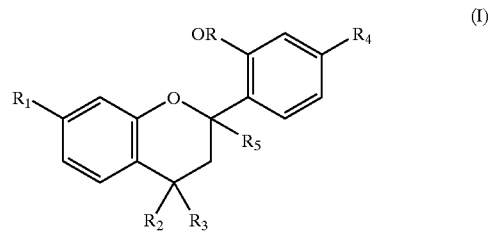

(wherein $R_1$, $R_2$, $R_3$, $R_4$, and $R_5$, independently represent a hydrogen atom or an alkyl group having 1 to 4 carbon atoms; and $R_7$ represents a sugar residue) and a pharmaceutically acceptable carrier.

2. The external agent for the skin as claimed in claim 1, comprising one or more compound(s) selected from the group consisting of a glucoside of inulavosin.

3. The external agent for the skin as claimed in claim 1, wherein said one or more compound(s) selected from the compounds represented by formula (I) is or are contained in an amount of 0.0005 to 10% by weight based on the total weight of the external agent.

4. The external agent for the skin as claimed in claim 1, wherein said agent is for whitening the skin.

5. A compound represented by formula (III) below:

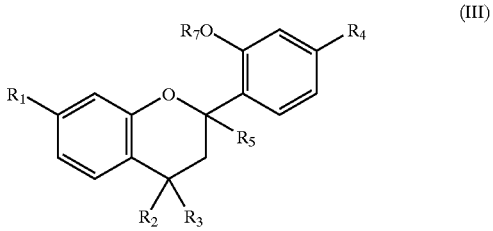

(wherein $R_1$, $R_2$, $R_3$, $R_4$, and $R_5$, independently represent a hydrogen atom or an alkyl group having 1 to 4 carbon atoms; and $R_7$ represents a sugar residue).

6. The compound as claimed in claim 5, wherein said compound is represented by formula (IV) below:

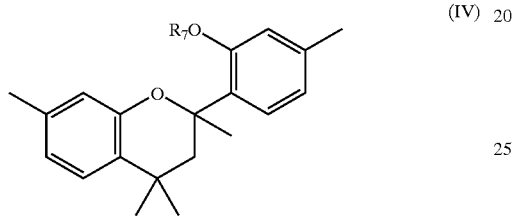

(wherein $R_7$ represents a sugar residue).

7. The compound as claimed in claim 6, wherein said compound is a glucoside of inulavosin.

8. A method of inhibiting or ameliorating skin pigmentation, comprising applying on a skin of a candidate for treatment a compound set forth in claim 1 in an effective amount.

9. A method of inhibiting or ameliorating skin pigmentation, comprising applying on a skin of a candidate for treatment a compound set forth in claim 2 in an effective amount.

10. A method of inhibiting or ameliorating skin pigmentation, comprising applying on a skin of a candidate for treatment a compound set forth in claim 3 in an effective amount.

11. A method of inhibiting or ameliorating skin pigmentation, comprising applying on a skin of a candidate for treatment a compound set forth in claim 4 in an effective amount.

12. A method of inhibiting or ameliorating skin pigmentation, comprising applying an a skin of a candidate for treatment a compound set forth in claim 5 in an effective amount.

13. A method of inhibiting or ameliorating skin pigmentation, comprising applying on a skin of a candidate for treatment a compound set forth in claim 6 in an effective amount.

14. A method of inhibiting or ameliorating skin pigmentation, comprising applying on a skin of a candidate for treatment a compound set forth in claim 7 in an effective amount.

15. A method of inhibiting or ameliorating skin pigmentation, comprising applying on a skin of a candidate for treatment a compound in an effective amount, wherein the compound is represented by formula (I) below:

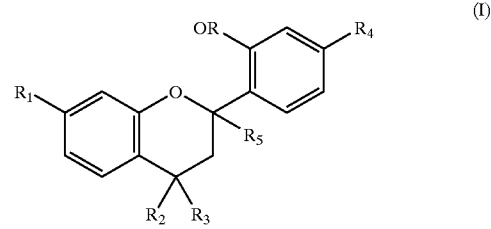

(wherein $R_1$, $R_2$, $R_3$, $R_4$, and $R_5$, independently represent a hydrogen atom or an alkyl group having 1 to 4 carbon atoms; and R represents a hydrogen atom, an acyl group, or a sugar residue).

16. A method of inhibiting or ameliorating skin pigmentation, comprising applying on a skin of a candidate for treatment a compound in an effective amount, wherein the compound is represented by formula (II) below:

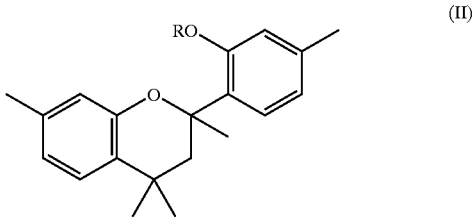

(wherein R represents a hydrogen atom, an acyl group represented by $R_6$—CO—, or a sugar residue; in which $R_6$ represents an alkyl group having 1 to 17 carbon atoms or an alkenyl group having one or two double bonds and 3 to 17 carbon atoms).

17. A method of inhibiting or ameliorating skin pigmentation, comprising applying on a skin of a candidate for treatment a compound in an effective amount, wherein the compound is selected from the group consisting of inulavosin, acetylinulavosin, and glucosides of inulavosin.

18. A method of inhibiting or ameliorating skin pigmentation, comprising applying on a skin of a candidate for treatment a compound set forth in claim 15 in an effective amount, wherein the compound is contained in an amount of 0.0005 to 10% by weight based on the total weight of an external agent which comprises the compound and a pharmaceutically acceptable carrier.

19. A method of inhibiting or ameliorating skin pigmentation, comprising applying on a skin of a candidate for treatment a compound set forth in claim 16 in an effective amount, wherein the compound is contained in an amount of 0.0005 to 10% by weight based on the total weight of an external agent which comprises the compound and a pharmaceutically acceptable carrier.

20. A method of inhibiting or ameliorating skin pigmentation, comprising applying on a skin of a candidate for treatment a compound set forth in claim 17 in an effective amount, wherein the compound is contained in an amount of 0.0005 to 10% by weight based on the total weight of an external agent which comprises the compound and a pharmaceutically acceptable carrier.

21. A method of inhibiting or ameliorating skin pigmentation, comprising applying on a skin of a candidate for treatment a compound in an effective amount, wherein the compound is represented by formula (III) below:

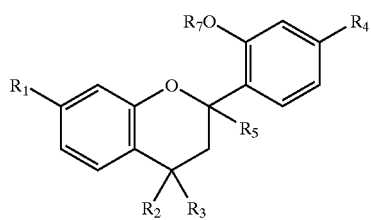 (III)

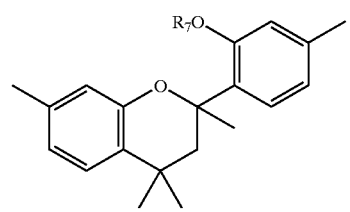 (IV)

(wherein $R_1$, $R_2$, $R_3$, $R_4$, and $R_5$, independently represent a hydrogen atom or an alkyl group having 1 to 4 carbon atoms; and $R_7$ represents an acyl group or a sugar residue).

22. A method of inhibiting or ameliorating skin pigmentation, comprising applying on a skin of a candidate for treatment a compound in an effective amount, wherein the compound is represented by formula (IV) below:

(wherein $R_7$ represents an acyl group represented by $R_8$—CO—, or a sugar residue; in which $R_8$ represents an alkyl group having 1 to 17 carbon atoms or an alkenyl group having one or two double bonds and 3 to 17 carbon atoms).

23. A method of inhibiting or ameliorating skin pigmentation, comprising applying on a skin of a candidate for treatment a compound in an effective amount, wherein the compound is acetylinulavosin or a glucoside of inulavosin.

* * * * *

UNITED STATES PATENT AND TRADEMARK OFFICE
CERTIFICATE OF CORRECTION

PATENT NO.   : 6,495,524 B1
DATED        : December 17, 2002
INVENTOR(S)  : T. Hattori et al.

It is certified that error appears in the above-identified patent and that said Letters Patent is hereby corrected as shown below:

Title page,
Item [57], ABSTRACT,
Formula (I) 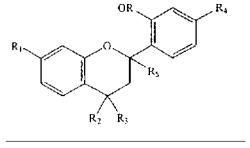 should be changed to -- 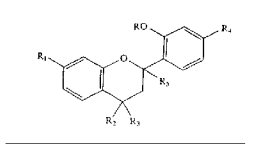 --

Column 12,
Line 38, "compounds)" should be changed to -- compound(s) --
Line 41, Formula (I)

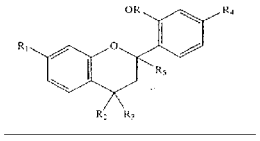

should be changed to -- 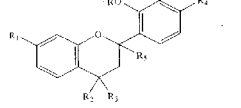 --

Line 54, "$R_7$ represents" should be changed to -- R represents --

Column 13,
Line 52, "applying an a skin" should be changeed to -- applying on a shin --

UNITED STATES PATENT AND TRADEMARK OFFICE
CERTIFICATE OF CORRECTION

PATENT NO.   : 6,495,524 B1
DATED        : December 17, 2002
INVENTOR(S)  : T. Hattori et al.

It is certified that error appears in the above-identified patent and that said Letters Patent is hereby corrected as shown below:

Column 14,
Line 1, Formula (I)

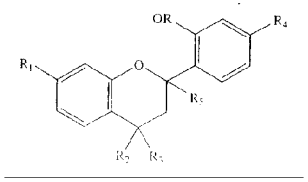

should be changed to

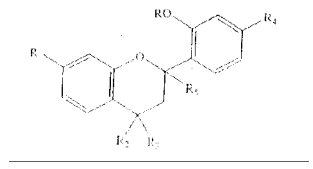

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,495,524 B1
DATED : December 17, 2002
INVENTOR(S) : T. Hattori et al.

It is certified that error appears in the above-identified patent and that said Letters Patent is hereby corrected as shown below:

<u>Column 13,</u>
Line 52, "applying on a shin" should be changed to -- applying on a skin --

Signed and Sealed this

Ninth Day of November, 2004

JON W. DUDAS
*Director of the United States Patent and Trademark Office*